United States Patent [19]

Chapman

[11] 4,174,357

[45] * Nov. 13, 1979

[54] ALKYLATION PROCESS

[75] Inventor: Charles C. Chapman, Bartlesville, Okla.

[73] Assignee: Phillips Petroleum Company, Bartlesville, Ohio

[*] Notice: The portion of the term of this patent subsequent to May 18, 1993, has been disclaimed.

[21] Appl. No.: 654,434

[22] Filed: Feb. 2, 1976

Related U.S. Application Data

[63] Continuation of Ser. No. 462,877, Apr. 22, 1974, Pat. No. 3,957,901, which is a continuation-in-part of Ser. No. 276,096, Jul. 28, 1972, abandoned.

[51] Int. Cl.² ............................................. C07C 3/52
[52] U.S. Cl. ....................................... 585/701; 585/14; 585/955
[58] Field of Search ............ 260/683.4, 683.43, 683.48; 208/17

[56] References Cited

U.S. PATENT DOCUMENTS

| | | | |
|---|---|---|---|
| 2,204,215 | 6/1940 | Greensfelder et al. | 208/17 |
| 3,060,116 | 10/1962 | Hardin, Jr. et al. | 260/683.4 R |
| 3,332,856 | 7/1967 | Hart | 208/17 |
| 3,548,023 | 12/1970 | Mayhue | 260/683.4 R |
| 3,647,905 | 3/1972 | Chapman | 260/683.4 R |
| 3,763,022 | 10/1973 | Chapman | 260/683.48 |
| 3,957,901 | 5/1976 | Chapman | 260/683.4 R |

*Primary Examiner*—George Crasanakis

[57] ABSTRACT

The bottom effluent from an isostripper of an HF alkylation system is combined with the bottom effluent consisting essentially of isopentanes and heavier hydrocarbons from a debutanizer column such as to produce an alkylate product stream under the provision that the mixing of the two streams is achieved in response to a signal representing the vapor pressure of the mixed streams.

2 Claims, 2 Drawing Figures

ALKYLATION PROCESS

This application is a continuation of my copending application, Ser. No. 462,877, filed Apr. 22, 1974 which issued as U.S. Pat. No. 3,957,901, which in turn is a continuation-in-part of my copending application Ser. No. 276,096, filed July 28, 1972, now abandoned.

BACKGROUND OF THE INVENTION

In an alkylation fractionation system, it is desirable that the resultant deisobutanized alkylate product stream have a preselected vapor pressure. In addition, it is desirable that the external heat consumed in the fractionation be as low as possible.

THE INVENTION

It is thus one object of this invention to provide a process for the production of an alkylate.

A further object of this invention consists in the provision of a debutanized alkylate having a controlled vapor pressure.

Still another object of this invention is to provide a process for the production of an alkylate gasoline which process has a low consumption of external energy.

Figure 1:
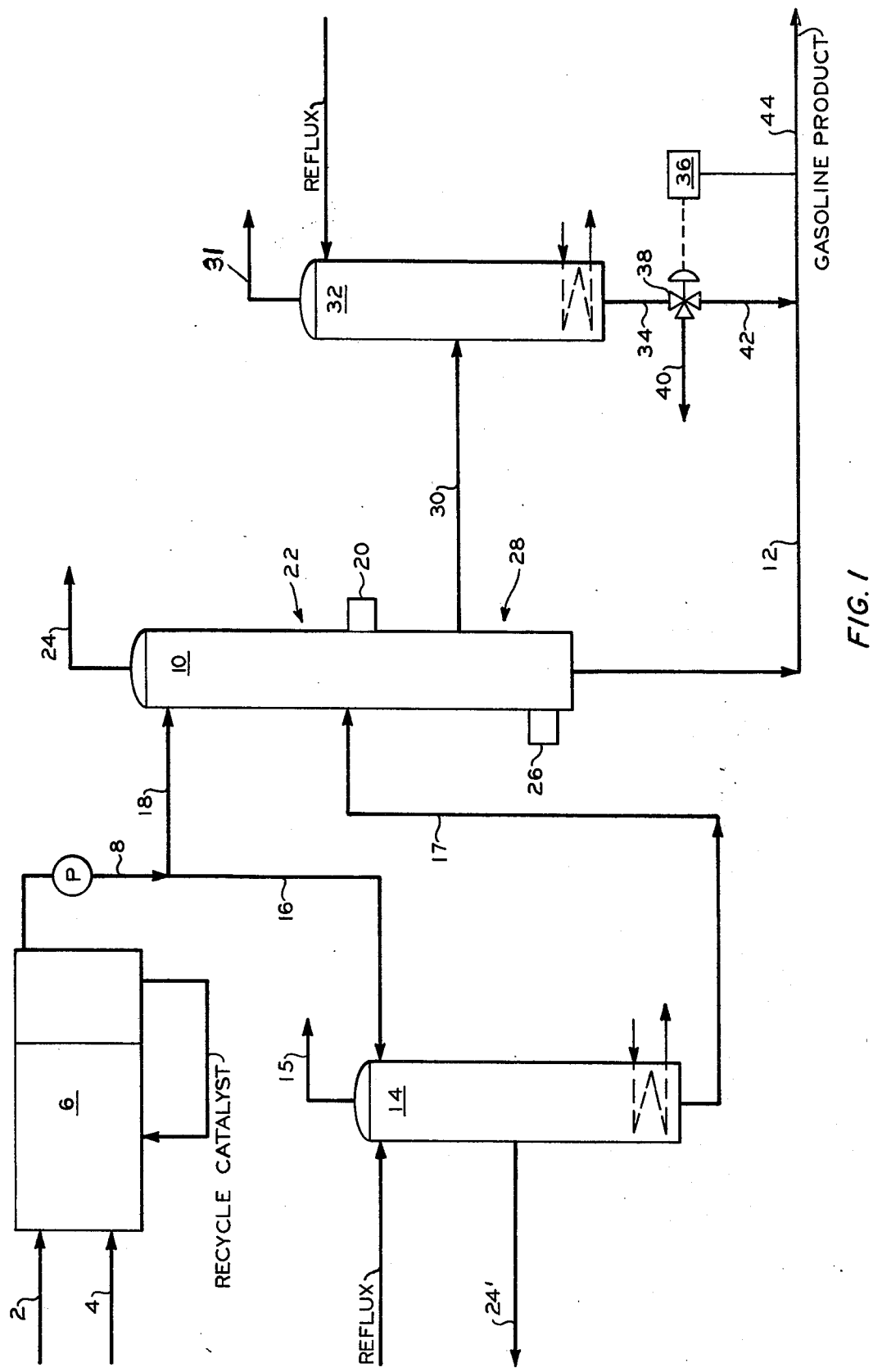
Figure 2:
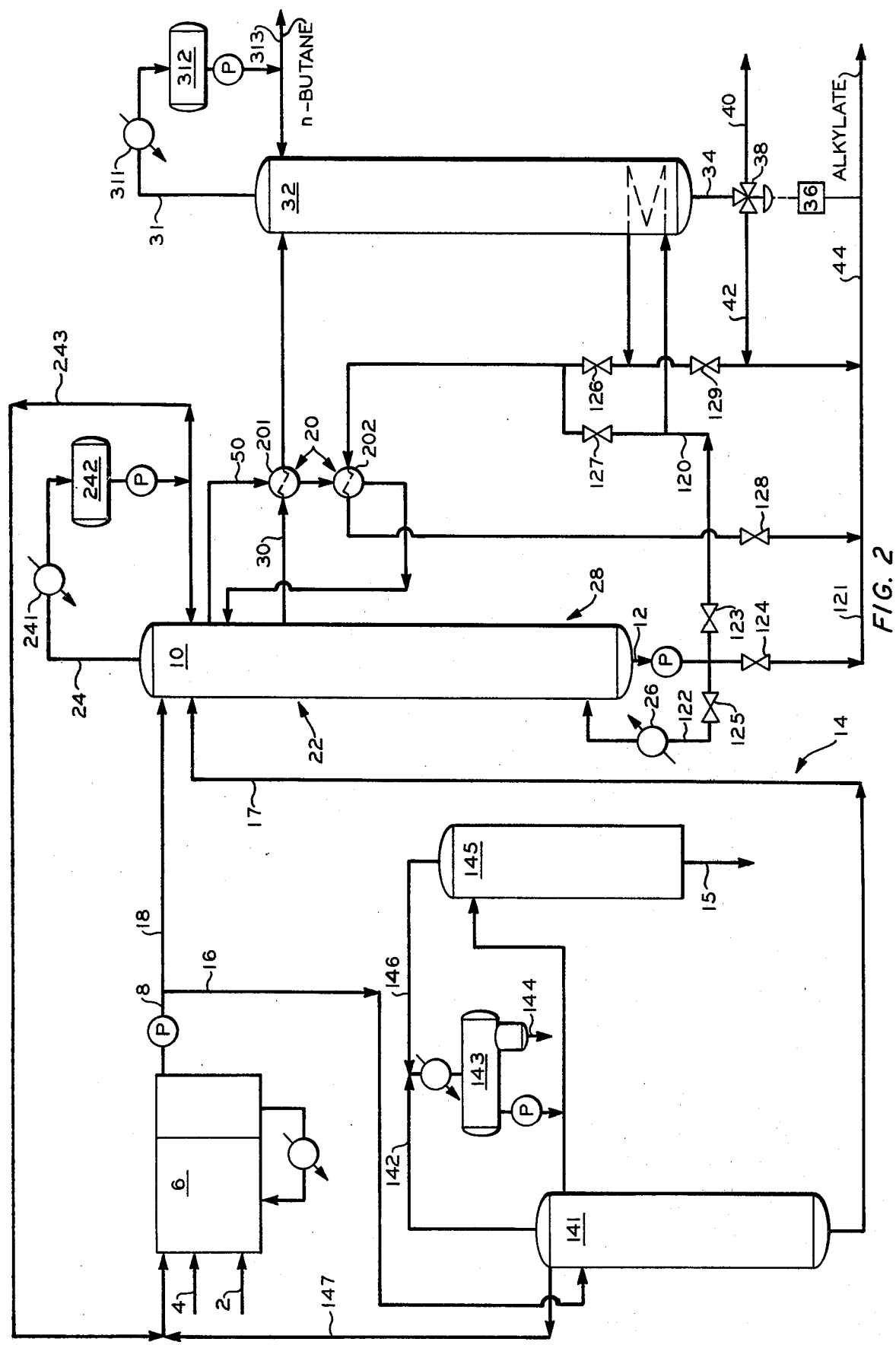

Other aspects, objects and advantages of the present invention will become apparent from the following disclosure of preferred embodiments, the appended claims and the drawing, in which FIG. 1 is a diagrammatic view of an alkylation and fractionation system and FIG. 2 is a diagrammatic view of the system shown in FIG. 1 including additional details.

In accordance with this invention, I have found a process for forming an alkylate product stream having a preselected vapor pressure comprising the steps of introducing an olefin stream and an isobutane stream into a reaction zone, reacting said components in the presence of a catalyst and thus forming a resultant product stream, introducing said product stream into an isobutane stripping zone, separating isobutane from the resultant product stream in said isobutane stripping zone, withdrawing an alkylate product stream from said isobutane stripping zone, withdrawing a side stream comprising normal butane and isopentane vapor from said isobutane stripping zone, introducing said side stream into a debutanizing column, removing normal butane from said side stream in said debutanizing column thus forming a resultant material, and controllably adding the resultant material to the alkylate product stream thus forming an alkylate product stream having a preselected vapor pressure.

Further details of this invention will become apparent from the following detailed description of the drawings and the examples.

Referring now to FIG. 1 of the drawing, an olefin feed stream 2 and an isobutane feed stream 4 are passed into and reacted in an alkylation reactor 6 to form a resultant product stream 8. The resultant hydrocarbon product stream 8 is passed into a deisobutanizing zone 10 at which location isobutane 24 for recycle is removed therefrom for forming an alkylate product stream 12, the isobutane being recycled to reactor 6.

The resultant product stream 8 discharging from this reactor 6 can be further processed prior to having isobutane removed therefrom. For example, and as shown in U.S. Pat. No. 3,647,905, the resultant product stream 8 can be split into first and second stream portions 16, 18.

The first portion 16 is passed into a depropanizing zone 14 at which location propane is removed via 15 therefrom, and the depropanized resultant product 17 and the second stream portion 18 are passed into the deisobutanizing zone 10, stream 18 functioning also as reflux for column 10. Recycle isobutane is recovered via conduit 24'.

The deisobutanizing zone 10 has a heating zone 20 provided in the middle portion 22 of the zone 10. An isobutane stream 24 is separated therefrom and discharged from the deisobutanizing zone 10 for recycle in the system, for example. A reboiler 26 is associated with a lower portion 28 of the zone 10. The alkylate product stream 12 is discharged from the lower portion 28 of the zone 10 and a stream 30 comprising normal butane vapor rich in isopentane can be removed from a locus near the heating zone 20. Stream 30 can be passed into a debutanizing zone 32 at which location normal butane 31 is separated from the stream 30 and the resultant material 34, comprising isopentane is discharged from the debutanizer and added to the alkylate product stream 12 for controlling the vapor pressure of said stream 12.

It should be understood, however, that the material 34 utilized in this invention for controlling the vapor pressure can be provided by other means.

An analyzer 36 can be associated with the alkylate product stream 12 at a location downstream of the locus at which the resultant material 34 is added for measuring the vapor pressure, delivering a signal in response to that analysis, and controlling the addition of the resultant material 34 in response to the signal by, for example, controlling a three-way control valve 38.

It is desirable to maintain the Reid vapor pressure at a value dependent upon the season and geographic location. In winter, this may be in the range of about 10 to about 14 psi. In the summer, this vapor pressure may be in the range of about 5 to 8 psi. At pressures above about 12 psi, for example, the three-way valve can cause the resultant material 34 to be discharged through line 40 as opposed to passing the material 34 into the stream 12 via line 42. In operation, the valve 38 would generally be throttling and passing material 34 into each of lines 40 and 42.

As is known in the art, it is desirable to maintain the vapor pressure of the product 12 within preselected limits. Product alkylate of desired preselected vapor pressure is removed via 44.

A calculated example of the process of this invention carried out in a system as shown in FIG. 1 is as follows:

EXAMPLE I

| | |
|---|---|
| Olefin Feed (2) (includes propane & butanes) (13% $C_3=$, 28% $C_4=$, 26% isobutane) | 35,900 B/D |
| Isobutane Feed (4) | 9,800 B/D |
| Recycle Isobutane (24) and (24') | 214,000 B/D |
| Isobutane from HF Rerun | 5,000 B/D |
| Hydrocarbon Stream (8) | 258,000 B/D |

| Components | Vol. % |
|---|---|
| Propane | 8 |
| Isobutane | 70 |
| Normal Butane | 7 |
| Isopentane (plus) | 15 |
| Total | 100 |

| | |
|---|---|
| Feed to Tower (14) via (16) | 96,800 B/D |
| Feed to Tower (10) via (18) | 161,200 B/D |
| Feed to Tower (10) via (17) | 29,470 B/D |
| Alkylate Yield (12) | 30,150 B/D |
| Reid Vapor Pressure | 6 psi |

-continued

| | | | |
|---|---|---|---|
| Vapor Feed to Tower (32) via (30) | | | 4,320 B/D |
| Components | Vol. % | | |
| Isobutane | 4 | | |
| Normal Butane | 74 | | |
| Isopentane (plus) | 22 | | |
| | Total | 100 | |
| LPC Normal Butane (93% nC₄) | | | 2,450 B/D |
| Flow from (42) into Alkylate (12) | | | 1,910 B/D |
| Components | Vol. % | | |
| Normal Butane | 2 | | |
| Isopentane (plus) | 98 | | |
| | Total | 100 | |
| Product Alkylate | | | 32,060 B/D |
| Reid Vapor Pressure | | | 7.5 psi |
| Operating Conditions: | | | |
| Alkylation Zone 6 | | | |
| Pressure, psi | | | 130 |
| Temperature, °F. | | | 90 |
| Depropanizer 14 | | | |
| Pressure, psi | | | 285 |
| Temperature, °F. | | | |
| Top | | | 126 |
| Bottom | | | 260 |
| Isobutane Stripper 10 | | | |
| Pressure, psi | | | 120 |
| Temperature, °F. | | | |
| Top | | | 150 |
| Middle | | | 170 |
| Bottom | | | 330 |
| Debutanizer 32 | | | |
| Pressure, psi | | | 85 |
| Temperature, °F. | | | |
| Top | | | 145 |
| Bottom | | | 215 |

In FIG. 2 a diagrammatic view of a system for producing an alkylate product stream is shown. The basic elements are the same as in the system shown in FIG. 1. In the following, therefore, only the additional features are described.

The depropanizer system comprises a depropanizing column 141 and an HF stripper 145. The portion 16 of the product stream 8 coming from phase separation zone of the reactor 6 which is to be depropanized is introduced into the depropanizing column 141. The liquid effluent of this column 141 is introduced as stream 17 into the isobutane stripper 10. The gaseous effluent 142 of the depropanizing column 141 containing propane and HF compounds is cooled to a temperature around 100° F. or so, so that the gases liquefy under the existing pressure. The liquefied gases are collected in an accumulator 143. The separate HF liquid portion of this accumulated liquid is withdrawn as stream 144 to be recycled with the HF catalyst into the reactor 6. The hydrocarbon liquid stream is pumped partially into the depropanizing column 141 as reflux and partially into an HF stripper unit 145. The liquid effluent 15 of this HF stripper contains mostly propane whereas the gaseous effluent 146 contains HF and some propane. This gaseous effluent is cooled together with the stream 142 and is introduced into the accumulator 143. A liquid side stream 147 containing isobutane and propane is withdrawn from the upper portion of the depropanizer 141. This stream is reintroduced into reactor 6.

The gaseous effluent 24 coming from the isobutane stripper 10 is cooled at 241 and the liquid formed (mainly isobutane) under existing pressure is collected in an accumulator 242. This liquid is partly pumped as reflux into the isobutane stripper 10 and is partly recycled via 243 into the reactor 6.

From an intermediate position of the isobutane stripper 10 a liquid stream 50 is heated in two heat exchangers 201 and 202. The first heat exchanger utilizes part of the thermal energy of the side stream effluent 30 comprising n-butane and pentane. The larger amount of heat, however, is transferred to stream 50 in the second heat exchanger 202 which utilizes part of the thermal heat of a portion 120 of the liquid effluent 12 of the isobutane stripper 10. The quantity of liquid effluent 120 employed is controlled by a control valve 123. The stream 120 can also serve as a heat source for the reboiling of the debutanizer 32. This heating operation, again, can be accomplished in parallel (valve 126 closed, valve 127 open) or in series (valve 126 open, valve 127 closed) with the heating step in heat exchanger 202. Valves 128 and 129 are provided to shut off the flow of stream 120 through heat exchanger 202 or the heating system of the debutanizer 32.

The liquid effluent 12 of the isobutane stripper 10 can be split up into three streams 120, 121 and 122. Stream 120 serves for the heating operations described above. Stream 121 is part of the alkylate product stream 44. Stream 122 is the portion of the liquid effluent 12 which is recycled and reboiled in reboiler 26 and reintroduced into the isobutane stripper 10. Valves 124 and 125 control the quantity of liquid in streams 121 and 122, respectively. Valve 124 can be closed completely if all the liquid effluent 12 which is not reboiled in reboiler 26 is used for heat exchange purposes in heat exchanger 202 and/or debutanizer 32.

The stream 50 withdrawn at an intermediate position of the isobutane stripper 10 and heated in the heat exchanger 201 and 202 is reintroduced into the isobutane stripper 10 at a location close to the point of its withdrawal, preferably just below this point. The liquid side stream 50 is partly vaporized by the heat exchange operations so that part of this stream when reintroduced into the isobutane stripper 10 moves in upward direction as a vapor, and part of it moves in downward direction as a liquid. Thus, by using the waste heat of the product stream 12, the amount of liquid which otherwise would have to be reboiled in reboiler 26 is considerably reduced.

The gaseous effluent 31 of the debutanizer 32 is cooled at 311 and the liquid formed (mainly n-butane) under the existing pressure is collected in an accumulator 312. This liquid is partly refluxed into the upper portion of debutanizer 32 and is partly withdrawn via line 313.

A calculated example of the process of this invention carried out in a system shown in FIG. 2 is the following:

EXAMPLE II

The figures in parentheses refer to the streams of FIG. 2.

| | | | |
|---|---|---|---|
| (2) | Olefin feed | | 35,870 B/D |
| | volume % C₃= | 13 | |
| | volume % C₄= | 22 | |
| | volume % isobutane | 26 | |
| | volume % amylenes | 7 | |
| | volume % isopentane | 18 | |
| | volume % normal butane | 7 | |
| | volume % propane | 7 | |
| | | 100 | |
| (4) | Isobutane feed | | 9,800 B/D |
| (243) | Isobutane recycle | | 156,200 B/D |
| | Isobutane from HF rerun (not shown) | | 3,700 B/D |
| (147) | Isobutane from depropanizor side draw | | 55,400 B/D |

-continued

|  |  |  |  |
|---|---|---|---|
|  | (Note: The isobutane usually comprises 82% of isobutane and 18% of other components.) |  |  |
| (8) | Hydrocarbon product stream |  | 250,200 B/D |
|  | volume % propane | 8.5 |  |
|  | volume % isobutane | 70.0 |  |
|  | volume % n-butane | 7.0 |  |
|  | volume % isopentane and heavier | 14.5 |  |
|  |  | 100 |  |
| (16) | Hydrocarbon stream to depropanizer |  | 89,000 B/D |
| (17) | Hot depropanizer bottoms to isobutane stripper |  | 29,479 B/D |
| (18) | Direct stream from reactor to isobutane stripper |  | 161,200 B/D |
| (15) | Propane yield |  | 3,600 B/D |
| (50) | Liquid side draw from isobutane stripper |  | 26,000 B/D |
|  | volume % normal butane | 80 |  |
|  | volume % isobutane | 20 |  |
| (30) | Vapor side draw |  | 4,320 B/D |
|  | volume % normal butane | 53 |  |
|  | butane % isobutane | 3 |  |
|  | butane % isopentane and heavier | 44 |  |
|  |  | 100 |  |
| (313) | Normal butane yield |  | 2,410 B/D |
| (34) | Isopentane and heavier yield |  | 1,910 B/D |
| (120) | Alkylate yield |  | 30,150 B/D |
|  | 120 (202) alkylate stream into interheater 202 |  | 24,910 B/D |
|  | 120 (32) alkylate stream to reboiler debutanizer 32 |  | 5,240 B/D |
|  | (Note: The two streams to heat the interheater 202 and the reboiler of the debutanizer 32 are in parallel.) |  |  |
| (121) | Direct alkylate product stream |  | 0 B/D |
| (42) | Isopentane and heavier stream |  | 1,910 B/D |
|  | volume % isopentane | 97.5 |  |
|  | volume % n-butane | 2.5 |  |
| (44) | Resulting alkylate product stream |  | 32,060 B/D |
|  | (Note: All quantities given above are calculated figures and are to be understood as liquid quantities even if the streams partially or totally are vaporous streams.) |  |  |
| Operating conditions |  |  |  |
| Reactor: | 100° F. and pressure to maintain liquid phase. |  |  |
| Depropanizer: | Top temperature 13° F. Bottom temperature 263° F. Pressure 300 psig |  |  |
| Isobutane stripper: | Top temperature 148° F. Bottom temperature 330° F. Pressure 140 psia |  |  |
| Debutanizer: | Top temperature 144° F. Bottom temperature 215° F. |  |  |

-continued

|  |  |
|---|---|
|  | Pressure 105 psia |
| Reid vapor pressure of alkylate stream 120 | About 7 psi |
| final alkylate product stream 44: | About 8 psi |
| Temperature of the liquid side draw 50 at the location of withdrawal: | 176° F. |
| Temperature of the partially vaporized side draw after passing through heat exchangers 201 and 202: | 177° F. |

The temperature of the alkylate stream 120 passing through the interheater 202 changed from about 330° F. to about 200° F. The temperature of the alkylate stream 120 passing through the debutanizer changed from 330° F. to 240° F.

The interheating of the liquid side draw 50 by the waste heat of the alkylate stream 120 saves 576 million Btu per day as compared to a process not using the side draw 50 and thus having to reboil this additional material in the isobutane stripper bottom. By using a part of the alkylate product stream 120 to reboil the debutanizer, an additional 81.4 million Btu per day can be saved.

Reasonable variations and modifications can be made, or followed, in view of the foregoing disclosure, without departing from the spirit or scope thereof.

I claim:

1. In a process for producing an alkylate end product stream having a preselected vapor pressure comprising reacting an olefin stream and an isoparaffin stream to form a resultant alkylate product stream, separating said resultant alkylate product stream into an isoparaffin stream, an alkylate stream and a vapor stream comprising normal butane and isopentane, the improvement comprising separating said vapor stream comprising normal butane and isopentane into a normal butane stream and a resultant material stream comprising isopentane, controllably adding said resultant material stream comprising isopentane to said alkylate stream so as to form an alkylate end product stream, measuring the vapor pressure of said alkylate end product stream and generating a signal representative of this measurement, and controlling the addition of said resultant material stream comprising isopentane to said alkylate stream in response to said signal to produce an alkylate end product stream having a constant and preselected vapor pressure.

2. A process in accordance with claim 1 wherein said isoparaffin is isobutane and said olefin is selected from the group consisting of propylene, butylene and mixtures thereof.

* * * * *